United States Patent [19]

Meyer

[11] Patent Number: 4,542,222
[45] Date of Patent: Sep. 17, 1985

[54] BENZIMIDAZOLES

[75] Inventor: Hans R. Meyer, Binningen, Switzerland

[73] Assignee: Ciba-Ceigy Corporation, Ardsley, N.Y.

[21] Appl. No.: 332,396

[22] Filed: Dec. 18, 1981

[30] Foreign Application Priority Data

Dec. 29, 1980 [CH] Switzerland ............... 9611/80
Jul. 16, 1981 [CH] Switzerland ............... 4666/81

[51] Int. Cl.⁴ .................................. C07D 405/04
[52] U.S. Cl. .................................. 548/327
[58] Field of Search ........................ 548/327

[56] References Cited

U.S. PATENT DOCUMENTS

| | | | |
|---|---|---|---|
| 3,637,734 | 1/1972 | Harnisch | 548/327 |
| 3,940,417 | 2/1976 | Schläepfer | 548/327 |
| 4,001,138 | 1/1977 | Lohmann | 252/301.27 |
| 4,384,121 | 5/1983 | Meyer | 548/327 |

FOREIGN PATENT DOCUMENTS 0010063  9/1980  European Pat. Off. .
2807008  8/1978  Fed. Rep. of Germany .

Primary Examiner—Robert W. Ramsuer
Attorney, Agent, or Firm—Edward McC. Roberts

[57] ABSTRACT

The novel benzimidazoles have the formula

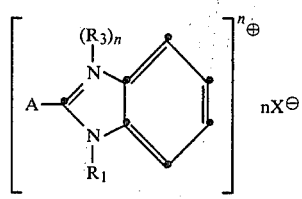

in which A is the radical

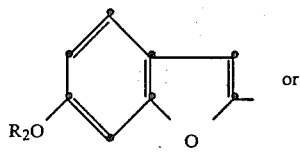

or

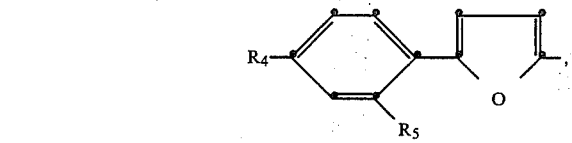

$R_1$ is cyanomethyl, 1-cyanoethyl or, if n is the number 1, also 2-cyanoethyl or $C_{3-6}$-carboalkoxymethyl, $R_2$ is $C_{1-4}$-alkyl or $C_{3-4}$-alkenyl, $R_3$ is cyanomethyl, cyanoethyl or $C_{3-6}$-carboalkoxymethyl, $R_4$ and $R_5$ independently of one another are hydrogen or chlorine, $X^\ominus$ is a colorless anion of an organic or inorganic acid and n is the number 0 or 1.

They are used for the fluorescent brightening of organic materials.

7 Claims, No Drawings

BENZIMIDAZOLES

The present invention relates to novel benzimidazoles which are unsubstituted on the benzo ring, to processes for their preparation and to their use for the fluorescent brightening of organic materials.

U.S. Pat. Nos. 3,637,734 and 4,009,994 and British Pat. No. 1,313,332 disclose the particularly readily accessible benzimidazoles which are unsubstituted on the benzo ring of the benzimidazole radical, but which produce unsatisfactory white effects. The non-quaternised representatives do not achieve high maximum effects. The quaternised or non-quaternised representatives which are unsubstituted on the benzo ring of the benzimidazole radical do not enable high white effects to be achieved.

It was therefore the object of the present invention to discover benzimidazoles which are unsubstituted on the benzo ring of the benzimidazole radical and which do not exhibit these drawbacks.

It has now been found that surprisingly high white effects can be achieved by means by some selected benzimidazoles which are unsubstituted on the benzo ring of the benzimidazole radical.

The novel benzimidazoles according to the invention have the formula

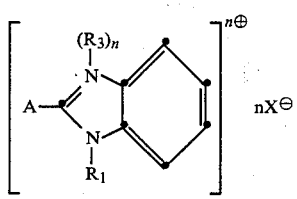

in which A is the radical

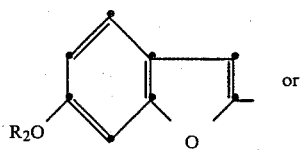

or

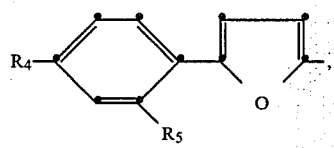

$R_1$ is cyanomethyl, 1-cyanoethyl or, if n is the number 1, also 2-cyanoethyl or $C_{3-6}$-carboalkoxymethyl, $R_2$ is $C_{1-4}$-alkyl or $C_{3-4}$-alkenyl, $R_3$ is cyanomethyl, cyanoethyl or $C_{3-6}$-carboalkoxymethyl, $R_4$ and $R_5$ independently of one another are hydrogen or chlorine, $X^\ominus$ is a colourless anion of an organic or inorganic acid and n is the number 0 or 1.

"$C_{3-6}$-Carboalkoxymethyl" is to be understood as meaning the radicals $C_4H_9OOCCH_2-$, $C_3H_7OOCCH_2-$, isomers thereof and, in particular, $C_2H_5OOCCH_2-$ and $CH_3OOCCH_2-$.

Compounds of the formula (1) in which n is 0 can also be in the form of acid adducts and can be used for fluorescent brightening.

A suitable anion $X^\ominus$ is any colourless anion of an organic or inorganic acid. Its nature has no essential influence on the fluorescent brightening properties of the compounds according to the invention. As a rule, the anion is introduced by the process of preparation (quaternisation or protonation), but it can also be replaced by another anion by known methods (see, for example, Houben-Weyl, Methoden der organischen Chemie ("Methods of Organic Chemistry"), Volume XI/2, pages 620–626). Anions of halogens can also be replaced in accordance with U.S. Pat. No. 4,095,943 by anions of aliphatic carboxylic acids by reacting the halide in the presence of these carboxylic acids using epoxides as hydrogen halide acceptors.

Within the scope of the compounds of the formula (1), those of the formula

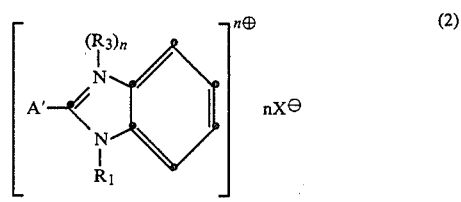

in which A' is the radical

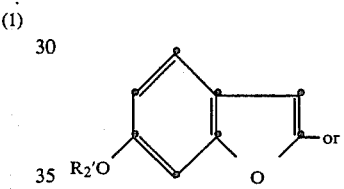

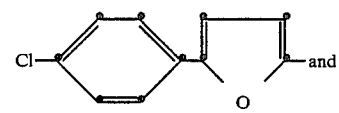

$R_2'$ is $C_{1-4}$-alkyl and $R_1$, $R_3$, $X^\ominus$ and n have the meaning indicated above, should be singled out. $R_2'$ is preferably methyl.

Within the scope of the compounds of the formulae (1) and (2), those of the formula

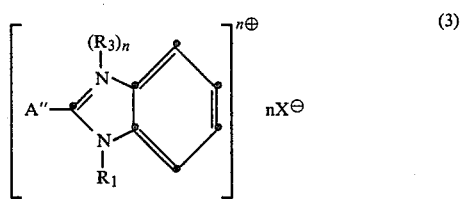

in which A" is the radical

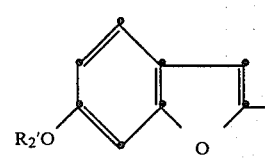

or, if n is the number 1, also the radical

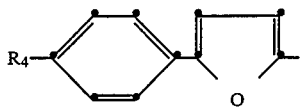

those of the formula

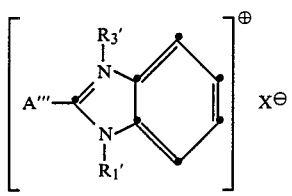

in which A''' is the radical

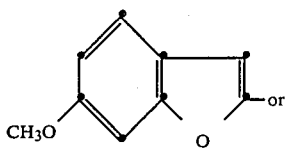

$R_1'$ and $R_3'$ independently of one another are cyanomethyl, cyanoethyl or $C_{3-8}$-carboalkoxymethyl, in which formulae $R_1$, $R_2'$, $R_3$, $R_4$, $X^\ominus$ and n have the meaning indicated above, and those of the formula

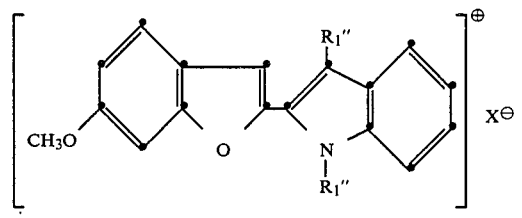

in which $R_1''$ is cyanoethyl or $C_{3-4}$-carboalkoxymethyl and $X^\ominus$ has the meaning indicated above, deserve special mention, $R_1'$ is preferably identical with $R_3'$.

Compounds of practical interest are those of the formula

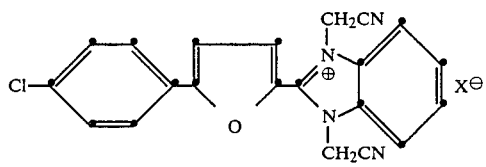

in which $X^\ominus$ is a colourless anion of an organic or inorganic acid,

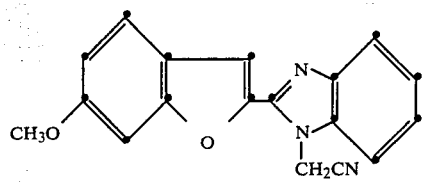

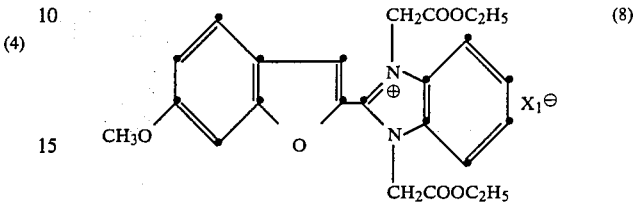

in which $X_1$ is chlorine or bromine, and

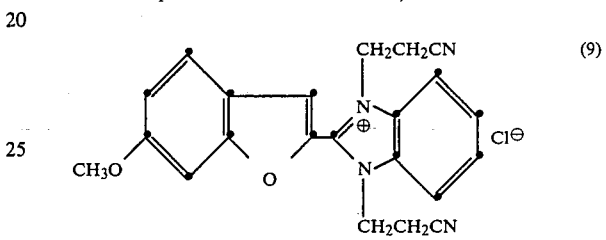

The benzimidazoles of the formula (1) are prepared by converting a benzimidazole of the formula

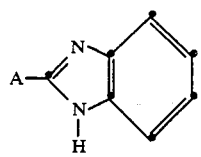

in a first stage, in the presence of a base, by means of at least one mol equivalent of an alkylating agent $R_1X$ or by means of acrylonitrile, into a benzimidazole of the formula

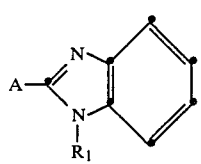

and, if desired, with or without previously isolating this compound, quaternising it in a second phase with a compound of the formula $R_3X$, A, $R_1$, $R_3$ and X in the above formulae having the meanings indicated above.

In the case of compounds of the formula (1) in which $R_1=R_3$, the alkylation and quaternisation can advantageously be carried out simultaneously, i.e. without isolating the compound of the formula (11).

Suitable bases are, in particular, alkali metal salts and alkaline earth metal salts of weak acids, such as sodium carbonate, potassium carbonate or calcium carbonate, or alkaline earth metal oxides, such as magnesium oxide, in a finely divided form. Tertiary amines which are difficult to quaternise, such as triisopropanolamine or 2,6-di-tert.-butylpyridine, are also suitable as acid acceptors.

A particular advantageous procedure is first to convert the benzimidazole of the formula (10) which is unsubstituted on the nitrogen, by means of strong alkalis, such as alkali metal hydroxides or alkali metal alcoholates, for example sodium hydroxide or sodium ethylate or potassium hydroxide or potassium ethylate, into the corresponding N-alkali metal salts, and then to alkylate the latter.

The alkylation or quaternisation is advantageously effected in a direct manner by warming in excess alkylating agent or in an inert solvent, at temperatures between 20° and 150° C., preferably 50° and 140° C., depending on the reactivity of the alkylating agent used.

In general, suitable reaction media in which the quaternisation can be carried out are any inert solvents. Preferred solvents are those which dissolve the starting material and from which the end product is precipitated immediately. The following may be mentioned as examples: aromatic hydrocarbons, such as benzene, toluene and xylene; halogenated hydrocarbons, such as trichloroethane, tetrachloroethylene, chlorobenzene or dichlorobenzene, and also nitro compounds, such as nitromethane, nitropropane or nitrobenzene, alkanols and open or cyclic ethers, such as butanol, dibutyl ether, ethylene glycol, ethylene glycol monomethyl ether, ethylene glycol monoethyl ether, anisole or dioxane; ketones, such as cyclohexanone or methyl ethyl ketone; fatty acid amides, such as dimethylformamide or dimethylacetamide; sulfoxides, such as dimethyl sulfoxide, and carboxylic acid esters, such as ethyl acetate or butyl acetate.

Quaternary compounds of the formula (1), i.e. those in which n is 1, are also obtained by reacting equivalent quantities of a coumarilyl halide or a phenyl-furane-carboxylic acid halide with N,N'-disubstituted o-phenylenediamines, for example N,N'-di-cyanoalkyl-o-phenylenediamines and N,N'-di-carboalkoxyalkyl-o-phenylenediamines. This process is particularly suitable for compounds of the formula (1) in which $R_1$ and $R_3$ are 2-cyanoethyl.

It is advantageous to carry out the reaction in inert solvents such as indicated above and/or in the presence of tertiary bases, such as pyridine or triethylamine, at temperatures between 20° and 150° C., preferably 50° and 140° C. For example, the compounds of the formula

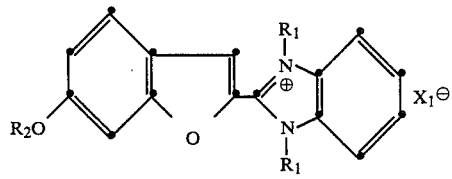

(12)

are prepared by this process by reacting a compound of the formula

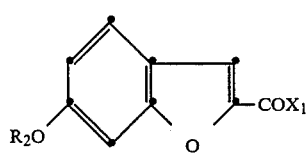

(13)

with a compound of the formula

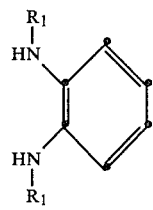

(14)

in which $X_1$ is halogen and $R_1$ and $R_2$ have the meanings indicated above. Preferred halogens are chlorine and bromine.

Compounds of the formula (1) in which A is alkoxybenzofuranyl or alkenyloxybenzofuranyl can also be prepared by subjecting a salicylaldehyde of the formula

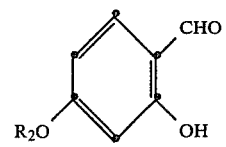

(15)

in which $R_2$ has the meaning indicated above, to a condensation reaction, in the presence or absence of a basic condensation agent, with a halogenomethylbenzimidazole of the formula

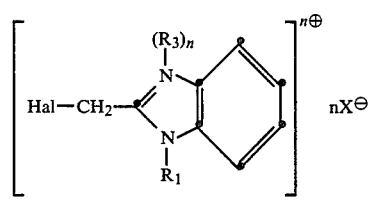

(16)

in which $R_1$, $R_3$, $X^\ominus$ and n have the meanings indicated above and Hal is fluorine, chlorine or bromine.

Suitable basic condensation agents are inorganic and organic compounds, such as alkali metal compounds and alkaline earth metal compounds, for example oxides, alcoholates, carbonates, bicarbonates or acetates, ammonium compounds, for example ammonium acetate, or tertiary amines, such as pyridine. It is preferable to use inorganic compounds of sodium and potassium, preferably carbonates thereof. However, it is also possible to use mixtures of various weakly basic compounds.

The quantity of condensation agent to be employed varies within wide limits. Although a catalytic quantity is adequate for the success of the reaction itself, it is advantageous to use equivalent quantities or even a multiple thereof.

It is advantageous to carry out the condensation reaction in a solvent which is inert under the reaction conditions. Suitable solvents of this type are apolar and dipolar aprotic solvents, such as xylene, dichlorobenzene, trichlorobenzene, dimethylformamide, diethylformamide, dimethylacetamide or N-methylpyrrolidone or mixtures thereof. It is preferable to use anhydrous organic solvents in which the base used is partly or completely soluble.

In certain cases, for example if the starting materials have low melting points and do not decompose, it is also possible to carry out the reaction according to the invention in the presence of the weakly basic condensation agent without a solvent, i.e. in the melt.

Depending on the process (with or without a solvent) and the compounds to be subjected to a condensation reaction, the reaction temperature can vary within a wide range. If solvents are used, it is between 50° C. and the boiling point of the particular solvent, preferably, however, between 50° and 200° C., and particularly between 90° and 160° C. If the condensation reaction is carried out without a solvent, the reaction temperature is then between the melting point of the mixture of reactants used and the decomposition temperature of the compounds to be subjected to the condensation reaction. Suitable temperatures are preferably between 100° and 250° C.

Preferred anions $X^{\ominus}$ are halides, such as chlorides or bromides, and also tosylates. If desired, the anion can be replaced by another anion in accordance with known methods (c.f., for example, Houben-Weyl, Methoden der organischen Chemie ("Methods of Organic Chemistry"), Volume XI/2, pages 620–626). In this case, preferred anions are anions of formic acid, acetic acid, propionic acid, glycollic acid, lactic acid, malic acid, tartaric acid, mucic acid, gluconic acid, citric acid, laevulinic acid, acrylic acid, methanephosphonic acid and monoalkyl esters thereof and of dialkyl esters of phosphoric acid.

The compounds of the formulae (10), (13), (14), (15) and (16) are known or can be prepared by methods which are known per se (c.f., for example, U.S. Pat. Nos. 3,637,734, British Pat. No. 1,313,332 and German Offenlegungsschriften Nos. 2,853,765 and 2,904,829).

The novel compounds defined above exhibit a more or less pronounced fluorescence in the dissolved or finely dispersed state. They can be used for the fluorescent brightening of a very wide variety of synthetic, semi-synthetic or natural organic materials or substances which contain such organic materials.

The following groups of organic materials, where fluorescent brightening thereof is relevant, may be mentioned as examples of the above, without the list given below being intended to express any restriction thereto;

I. Synthetic organic materials of high molecular weight:
  (a) Polymerisation products based on organic compounds containing at least one polymerisable carbon-carbon double bond, i.e. their homopolymers or copolymers as well as their after-treatment products, for example crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example ethylene, propylene, styrenes or dienes and also so-called ABS polymers) and polymers based on vinyl and vinylidene compounds (for example vinyl chloride, vinyl alcohol and vinylidene chloride),
  (b) Polymerisation products which can be obtained by ring opening, for example polyamides of the polycaprolactam type, and also polymers which are obtainable either by polyaddition or by polycondensation, such as polyethers or polyacetals,
  (c) Polycondensation products or precondensates based on bifunctional or polyfunctional compounds with condensable groups, the homocondensation and co-condensation products, and after-treatment products thereof, for example polyesters, in particular saturated polyesters (for example polyesters of ethylene glycol/terephthalic acid) or unsaturated polyesters (for example maleic acid/-dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones,
  (d) Polyaddition products, suc as polyurethanes (crosslinked and uncrosslinked).

II. Semi-synthetic organic materials, for example cellulose esters of varying degrees of esterification (so-called 2½-acetate or triacetate) or cellulose ethers, regenerated cellulose (viscose or cuprammonium cellulose), or their after-treatment products, and casein plastics III. Natural organic materials of animal or vegetable origin, for example based on cellulose or proteins, such as cotton, wool, linen, silk, varnish gums, starch and casein.

The organic materials which are to undergo fluorescent brightening can be in the most diverse states of processing (raw materials, semi-finished goods or finished goods). On the other hand, they can be in the form of structures of the most diverse shapes, for example predominantly three-dimensional structures, such as sheets, profiles, injection mouldings, various machined articles, chips, granules or foams, and also predominantly two-dimensional structures, such as films, foils, lacquers, coverings, impregnations and coatings, or predominantly one-dimensional bodies, such as filaments, fibres, flocks and wires. The said materials can, on the other hand, also be in an unshaped state, in the most diverse homogeneous or inhomogeneous forms of division, for example in the form of powders, solutions, emulsions, dispsersions, lactices, pastes or waxes.

Fibre materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds to be used in accordance with the invention are of importance, inter alia, for the treatment of organic textile materials, especially woven textile fabrics. If fibres, which can be in the form of staple fibres or endless filaments or in the form of hanks, woven fabrics, knitted fabrics, non-wovens, flocked substrates or bonded fabrics, are to be subjected to fluorescent brightening according to the invention, this is advantageously effected in an aqueous medium in which the particular compounds are present in a finely divided form (suspensions, so-called microdispersions, or, where appropriate, solutions). If desired, dispersing agents, stabilisers, wetting agents and further assistants can be added during the treatment.

Depending on the type of fluorescent brightening compound used, it can prove advantageous to apply the compounds in a neutral, alkaline or acid bath. The treatment is usually carried out at temperatures below about 20° and 140° C., for example at the boiling point of the bath or near it (about 90° C.). Solutions or emulsions in organic solvents can also be used for the finishing, according to the invention, of textile substrates, as is practised in the dyeing industry in so-called solvent dyeing (pad-thermofixation, or exhaust dyeing processes in dyeing machines).

The novel fluorescent brightening agents of the present invention can further be added to or incorporated in the materials before or during their shaping. Thus, for example, they can be added to the compression moulding composition or injection moulding composition during the production of films, sheets (for example incorporated in polyvinyl chloride in a roll mill at elevated temperature) or mouldings.

If the shaping of man-made fully synthetic or semi-synthetic organic materials is effected by spinning processes or from spinning solutions/melts, the fluorescent brightening agents can be applied by the following processes:

addition to the starting substances (for example monomers) or intermediates (for example precondensates or prepolymers), i.e. before or during the polymerisation, polycondensation or polyaddition, sprinkling in powder form on polymer chips or granules for spinning solutions/melts, bath dyeing of polymer chips or granules for spinning solutions/melts, metered addition to spinning melts or spinning solutions and application to the spun tow before stretching.

The novel fluorescent brightening agents of the present invention can, for example, also be employed in the following use forms:

(a) in mixtures with dyestuffs (shading) or pigments (coloured pigments or especially, for example, white pigments), or as an additive to dyebaths, printing pastes, discharge pastes or reserve pastes, or for the after-treatment of dyeings, prints or discharge prints, (b) in mixtures with carriers, wetting agents, plasticizers, swelling agents, antioxidants, light stabilisers, heat stabilisers and chemical bleaching agents (chlorite bleach or bleaching bath additives), (c) in admixture with crosslinking agents or finishing agents (for example starch or synthetic finishes), and in combination with a wide variety of textile finishing processes, especially synthetic resin finishes (for example creaseproof finishes such as "wash-and-wear", "permanent press" or "non-iron"), as well as flameproof finishes, soft-handle finishes, anti-soiling finishes or antistatic finishes, or antimicrobial finishes, (d) incorporation of the fluorescent brightening agents into polymeric carriers (polymerisation, polycondensation or polyaddition products) in dissolved or dispersed form, for use, in example, in coating agents, impregnating agents or binders (solutions, dispersions and emulsions) for textiles, non-wovens, paper and leather, (e) as additives to master batches, (f) as additives to a wide variety of industrial products in order to render these more marketable (for example improving the appearance of soaps, detergents and pigments), (g) in combination with other substances which have a fluorescent brightening action, (h) in spinning bath preparations, i.e. as additives to spinning baths which are used for improving the slip for the further processing of synthetic fibres, or from a special bath prior to stretching the fibre, (i) as scintillators for various purposes of a photographic nature, for example for electrophotographic reproduction or supersensitising, and (j) depending on the substitution, as laser dyes.

If the brightening process is combined with textile treatment or finishing methods, the combined treatment can in many cases advantageously be carried out with the aid of appropriate stable preparations which contain the fluorescent brightener compounds in such a concentration that the desired white effect is achieved.

In certain cases, the fluorescent brighteners are made fully effective by an after-treatment. This can be, for example, a chemical treatment (for example acid treatment), a heat treatment (for example heating) or a combined chemical/heat treatment. Thus, for example, the appropriate procedure to follow in fluorescent brightening a number of fibre substrates, for example polyester fibres, with the fluorescent brightening agents of the present invention, is to impregnate these fibres with aqueous dispersions (or, where appropriate, also solutions) of the fluorescent brightening agents at temperatures below 75° C., for example at room temperature, and to subject them to a dry heat treatment at temperatures above 100° C., it generally being advisable additionally to dry the fibrous material beforehand at a moderately elevated temperature, for example at not less than 60° C. to about 130° C. The heat treatment in the dry state is then advantageously carried out at temperatures between 120° C. and 225° C., for example by heating in a drying chamber, by ironing within the specified temperature range or by treatment with dry, superheated steam. Drying and the dry heat treatment can also be carried out in immediate succession or combined in a single operation.

The amount of the novel fluorescent brightening agents to be used according to the invention, based on the material to be subjected to fluorescent brightening, can vary within wide limits. A marked and lasting effect can be obtained even with very small amounts, in certain cases, for example, amounts of 0.0001 percent by weight. However, it is also possible to use amounts of up to about 0.8 percent by weight and, where necessary, of up to about 2 percent by weight. For most practical purposes, it is preferable to use amounts of between 0.0005 and 0.5 percent by weight.

For various reasons, it is often advantageous not to employ the fluorescent brighteners by themselves, i.e. pure, but in admixture with a very wide variety of assistants and extenders, for example sodium formate, sodium acetate or lactate.

The novel fluorescent brighteners of the formula (1) and subordinate formulae in which n is the number 1, have the particular advantage that they are resistant to chlorites.

In the examples, unless otherwise indicated, parts are always by weight and percentages are always by weight. Unless indicated otherwise, melting points and boiling points are uncorrected.

EXAMPLE 1

A mixture of 27.3 g of 2-benzimidazol-2'-yl-6-methoxy-benzofuran (c.f. British Pat. No. 1,313,332), 100 ml of chloroacetonitrile and 14.7 g of anhydrous ground potassium carbonate is stirred for 6 hours at reflux temperature. In the course of this, the starting material dissolves, after which the reaction product is precipitated. After being cooled to room temperature the mixture is filtered with suction and the residue is washed several times with isopropanol and water. This gives 19.3 g of the compound of the formula

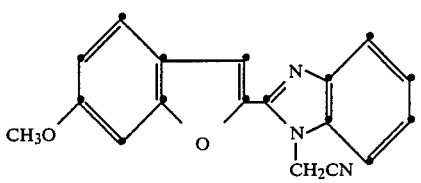

which is recrystallised from perchloroethylene and xylene (light yellow crystals of melting point 188°–91° C.).

The compounds of the formula

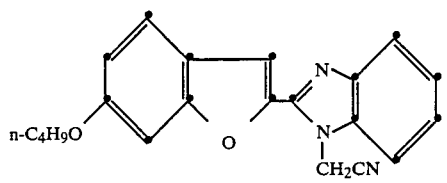

and

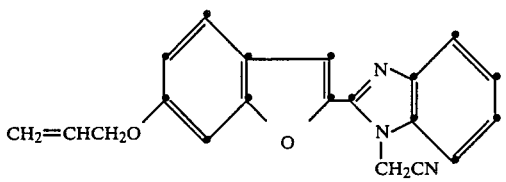

are obtained similarly.

EXAMPLE 2

The procedure described in Example 1 is repeated, using 60 ml of 2-bromoproprionitrile instead of chloroacetonitrile and adding a further 8.9 g of potassium carbonate in portions during the course of the reaction. The compound of the formula

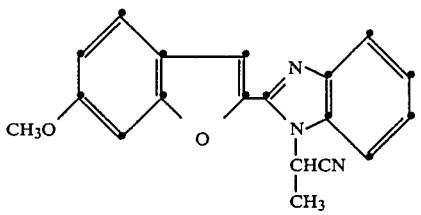

is obtained.

This compound is purified by being chromatographed over aluminium oxide of neutral activity 1, using ethylene chloride, followed by recrystallisation from isopropanol (melting point 72° C.).

EXAMPLE 3

19.8 g of a 30% strength solution of sodium methylate are added dropwise, while stirring, to a hot solution of 27.3 g of 2-benzimidazol-2'-yl-6-methoxy-benzofuran in 450 ml of methanol. The methanol is removed completely by distillation, finally in vacuo. 50 ml of ethyl bromoacetate are added to the solid residue, the suspension is stirred for 1 hour at 50° C. and diluted with 250 ml of methylene chloride after cooling to room temperature, and insoluble material is filtered off. The resulting solution is evaporated in vacuo and the residue is taken up in 450 ml of hot ethylene chloride. Cooling to 0° C. produces a thick precipitate of the product. This is filtered off, washed with ethylene chloride and dried in vacuo at 70° C. to give 33.5 g of the compound of the formula

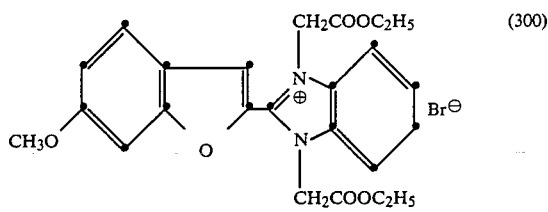

which, after recrystallisation from isopropanol, is obtained in the form of nearly colourless crystals of melting point 178°–180° C. (decomposition).

EXAMPLE 4

11 ml of a 10N aqueous solution of potassium hydroxide are added, at 70° C. and while stirring, to a suspension of 27.3 g of 2-benzimidazol-2'-yl-6-methoxy-benzofuran in 100 ml of ethanol, and the resulting solution is evaporated completely in vacuo. 50 ml of ethyl chloroacetate are added to the solid residue, the suspension is stirred for ½ hour at 130° C. and, after cooling, diluted with 100 ml of methylene chloride, and insoluble material is filtered off. The solution is evaporated in vacuo and the residue is taken up in 100 ml of warm acetone. The product is precipitated slowly on cooling the solution to 0° C. It is filtered off, washed with acetone and dried in vacuo at room temperature to give 10.2 g of the compound of the formula

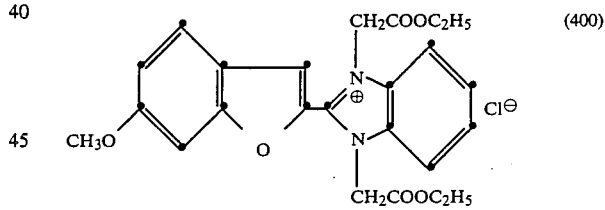

This compound can be recrystallised from acetone: melting point 153°–158° C. (decomposition).

EXAMPLE 5

A mixture of 27.3 g of 2-benzimidazol-2'-yl-6-methoxy-benzofuran, 80 ml of methyl chloroacetate and 15.2 g of anhydrous, ground potassium carbonate is stirred for 4 hours at 90° C., and insoluble material is filtered off while the mixture is still hot. The filtrate is evaporated completely in vacuo and the residue is taken up in 80 ml of warm methanol. After the solution has been cooled to 0° C., 50 ml of water are added, while stirring, whereupon the reaction product is precipitated gradually. It is filtered off with suction, washed several times with a 1:1 mixture of methanol and water and dried in vacuo over calcium chloride. Recrystallisation from carbon tetrachloride gives 23.0 g of the compound of the formula

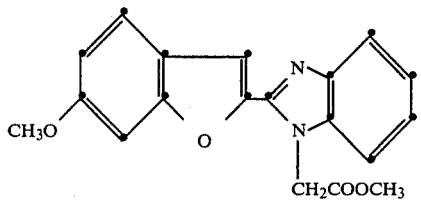

(500)

Melting point 111°–113° C. (from isopropanol).

8.4 g of this product are stirred in 20 ml of chloroacetonitrile for 2 hours at 120° C. and the solution is evaporated completely in vacuo on a rotary evaporator. The residue is taken up in 70 ml of chloroform and the product which has precipitated is filtered off with suction, washed with three times 20 ml of chloroform and dried in vacuo. This gives 7.7 g of the compound of the formula

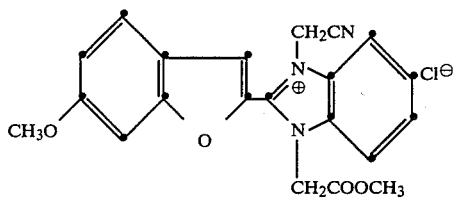

(501)

of melting point 150° C. (decomposition). The product can be recrystallised from ethanol.

EXAMPLE 6

A suspension of 4.2 g of 6-methoxy-coumarilyl chloride and 4.3 g of the compound of the formula

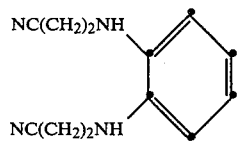

(600)

in 20 ml of pyridine is stirred for ½ hour at 100° C. The reaction product is precipitated on cooling the solution to 5° C. The product is filtered off with suction, washed several times with acetone and toluene and dried in vacuo at 100° C. This gives 5.9 g of the compound of the formula

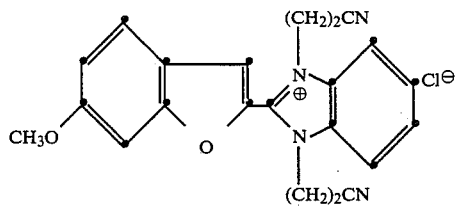

(601)

in the form of light yellow crystals of melting point 215°–216° C. (decomposition).

EXAMPLE 7

39.6 g of 2-benzimidazol-2'-yl-6-methoxybenzofuran are stirred in 180 ml of acrylonitrile and 18.5 g of triethylamine for 44 hours at reflux temperature. The triethylamine and the excess acrylonitrile are filtered off, the residue is dissolved in toluene and the solution is filtered while hot and allowed to cool. The product which has precipitated is filtered off with suction, washed with toluene and dried in vacuo at 100° C. This gives 43.2 g of the compound of the formula

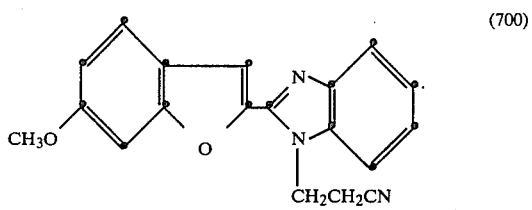

(700)

Melting point 131°–133° C. (after recrystallisation from toluene).

6.4 g of this product in 20 ml of chloroacetonitrile are heated at reflux temperature for 'hours. 80 ml of methyl ethyl ketone are added to the solution and the mixture is allowed to cool. The product which as crystallised out is filtered off with suction, washed several times with methyl ethyl ketone and dried in vacuo at 100° C. This gives 5.7 g of the compound of the formula

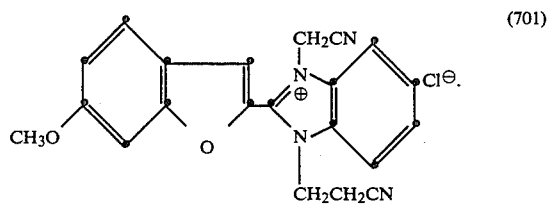

(701)

Melting point 195°–201° C. The compound can be recrystallised from isopropanol.

EXAMPLE 8

29.5 g of 2-benzimidazol-2'-yl-5-(p-chlorophenyl)-furan are dissolved by warming in 20 ml of methanol and 11 ml of 10N sodium hydroxide solution. The solution is evaporated completely in vacuo, 100 ml of chloroacetonitrile are added and the suspension is stirred for 4 hours at 70° C. After it has been cooled to room temperature, the suspension is diluted with 100 ml of methanol and 10 ml of water and is filtered, and the residue is washed several times with methanol and water. The residue is dried in vacuo at 100° C. (28.0 g) and is recrystallised from n-butanol. This gives 20.9 g of the compound

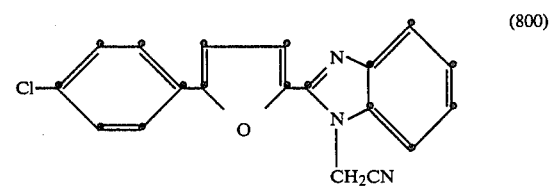

(800)

in the form of pale yellow crystals of melting point 233°–226° C. (from xylene).

6.7 g of this product are stirred in 20 ml of ethyl bromoacetate for 2 hours at 100° C. After the starting material has dissolved, a voluminous precipitate of the end product is formed. The mixture is diluted with 50 ml of methyl ethyl ketone and is filtered with suction at approx. 40° C., and the residue is washed with methyl ethyl ketone. Drying gives 7.3 g of the compound

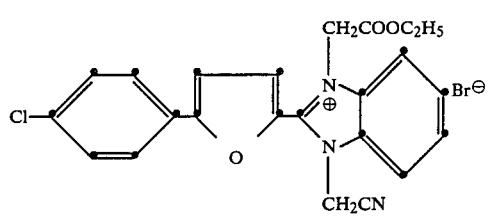
(801)

which is obtained in the form of light yellow crystals of melting point 170° C. (not sharp), after recrystallisation from water

EXAMPLE 9

5.9 g of 2-benzimidazol-2'-yl-5-(p-chlorophenyl)-furan and 3.3 g of anhydrous, ground potassium carbonate are stirred in 30 ml of chloroacetonitrile for 18 hours at reflux temperature. The excess chloroacetonitrile is distilled off in vacuo, the residue is extracted by boiling with 80 ml, and then 20 ml, of water, and the aqueous phases are decanted off at 100° C. The combined aqueous phases are clarified by filtration while hot, after adding active charcoal, and are concentrated somewhat, after which the product crystallises out on cooling. The product is filtered off with suction, washed with water and dried in vacuo at 100° C. This gives 1.8 g of the compound of the formula

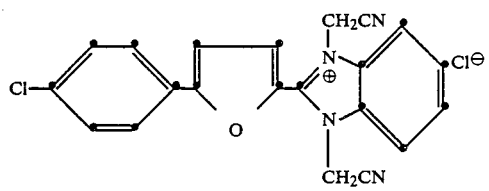
(900)

in the form of light yellow crystals which still contain ½ mol of water of crystallisation. Melting point 205°–207° C. (after recrystallisation from 3:7 alcohol/acetonitrile).

The procedure used in this example is repeated, using a corresponding quantity of 2-benzimidazol-2'-yl-5-phenylfuran instead of the furan derivative mentioned. The compound of the formula

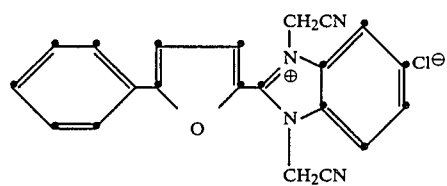
(901)

is obtained.
The compound of the formula

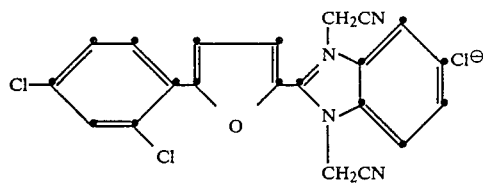
(902)

is obtained analogously.

EXAMPLE 10

The procedure used in Example 3 is repeated, using as the starting material 2-benzimidazol-2'-yl-5-(p-chlorophenyl)-furan instead of the 2-benzimidazol-2'-yl-6-methoxy-benzofuran mentioned. The compound of the formula

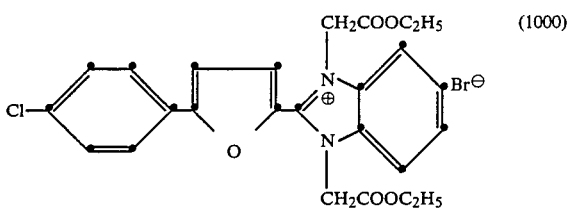
(1000)

is obtained.

EXAMPLE 11

7.0 g of 2-[1'-cyanoethyl-benzimidazol-2'-yl]-5-(p-chlorophenyl)-furan (c.f. U.S. Pat. No. 3,637,734) are stirred in about 30 ml of chloroacetonitrile for 8 hours at reflux temperature. The excess chloroacetonitrile is filtered off in vacuo, the residue is extracted by boiling with three times 40 ml of water and the aqueous phase is decanted off at 100° C. in each case. After adding active charcoal, the combined aqueous solutions are clarified by filtration while hot, after which the product crystallises out on cooling. It is filtered off with suction, washed with water and dried in vacuo at 100° C. This gives 5.2 g of the compound of the formula

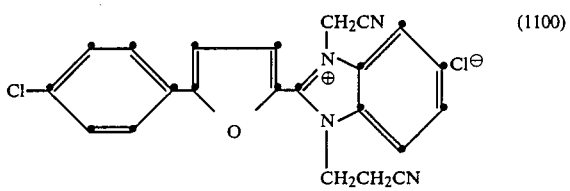
(1100)

Melting point 255° C. (after recrystallisation from n-propanol).

EXAMPLE 12

A polyacrylonitrile fabric (Orlon 75) is treated on a dyeing machine, at a liquor ratio of 1:20, with an aqueous liquor containing 0.1%, based on the weight of the goods, of a fluorescent brightener of the formula (100), (200), (300), (601), (701), (801), (900) or (1100), 1 g/l of an adduct of 35 mols of ethylene oxide and 1 mol of stearyl alcohol, and 1.5 ml/l of 85% strength formic acid. Application is carried out in accordance with the following temperature programme: 40°–97° C./30 minutes, 97° C./30 minutes and 97°–40° C./15 minutes. The polyacrylonitrile fabric is then rinsed for 30 seconds in running, softened water and is dried at 70° C. in a drying cabinet. The fabric treated in this way has a high white effect.

EXAMPLE 13

A modified polyacrylonitrile fabric (Courtelle) is treated on a dyeing machine, at a liquor ratio of 1:20, with an aqueous liquor containing 0.1%, based on the weight of the goods, of a fluorescent brightener of the formula (300), (601), (701), (900) or (1100), 1 g/l of oxalic acid, 0.25 g/l of a polyphosphate as a complex-forming agent and 0.125 g/l of sodium metabisulfite. Application is carried out in accordance with the following temperature programme: 40°–97° C./30 minutes, 97° C./30 minutes and 97°–40° C./15 minutes. The polyacrylonitrile fabric is then rinsed for 30 seconds in running, softened water and is dried at 70° C. in a drying cabinet. The fabric treated in this way has a good white effect.

EXAMPLE 14

A freshly spun, stretched, never-dried polyacrylonitrile tow (corresponding to a dry weight of 3.0 g) is immersed, while still moist, for 4 seconds at 45° C. in 100 ml of an aqueous liquor which contains 0.005% of a brightener of the formula (300), (601), (900) or (1100) and which has been adjusted to pH 4 with concentrated oxalic acid solution. The never-dried tow is then rinsed for a short time with water and is dried at 90° to 100° C. A polyacrylonitrile fibre which has a good white effect is obtained in this way. The dyeing can also be carried out, for example, at pH 6 (adjusted by adding sodium acetate). Increasing the temperature of the dyeing liquor, for example to 40° C., increases the rate of exhaustion.

Higher white effects are achieved by increasing the concentration of fluorescent brightener, for example to 0.005%.

EXAMPLE 15

An aqueous solution is prepared containing 0.3%, based on the weight of the material to be whitened, of a fluorescent brightener of the formula (300), (801) or (900). This solution is warmed to 30° C. A modified polyester fabric (®Dacron 64), prepared by co-condensation with 2 to 5 mol % of isophthalic acid 5-sodium sulfonate, is then put into the solution, a liquor ratio of 1:25 being maintained. The temperature is raised to 100° C. in the course of 10 minutes and the mixture is kept at this temperature for 20 minutes. It is then cooled to 50° C. in the course of 5 minutes. The fabric is then rinsed in running cold water and is subsequently dried at 180° C. with a flat-iron. It has a high white effect.

What is claimed is:

1. A benzimidazole of the formula

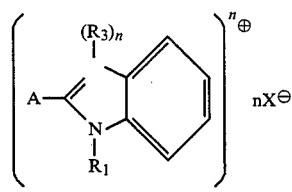

in which A is the radical

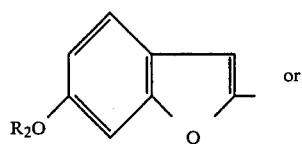

-continued

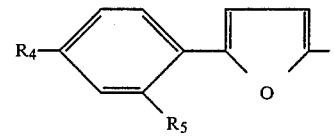

$R_1$ is cyanomethyl, 1-cyanoethyl or 2-cyanoethyl, $R_2$ is $C_{1-4}$-alkyl, $R_3$ is cyanomethyl, cyanoethyl or $C_{3-6}$-carboalkoxymethyl, $R_4$ and $R_5$ independently of one another are hydrogen or chlorine, $X^-$ is a colorless anion of an organic or inorganic acid and n is the number 0 or 1, provided that when n is 0, $R_1$ is cyanomethyl or 1-cyanoethyl, and provided that when A is

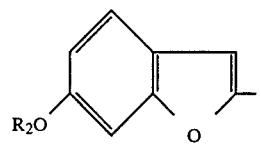

and $R_1$ is cyanoethyl, $R_3$ is not cyanomethyl.

2. A benzimidazole according to claim 1 of the formula

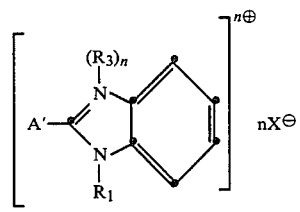

in which A' is the radical

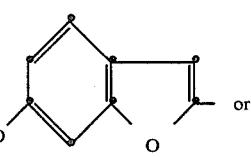

or

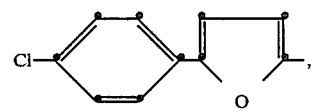

$R_1$ is cyanomethyl, 1-cyanoethyl or, if n is the number 1, also 2-cyanoethyl, $R_2'$ is $C_{1-4}$-alkyl, $R_3$ is cyanomethyl, cyanoethyl or $C_{3-6}$-carboalkoxymethyl, $X^\ominus$ is a colourless anion of an organic or inorganic acid and n is the number 0 or 1.

3. A benzimidazole according to claim 1 of the formula

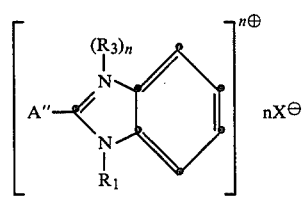

in which A″ is the radical

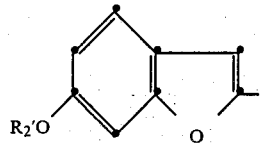

or, if n is the number 1, also the radical

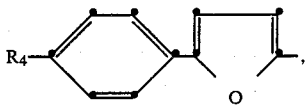

R₁ is cyanomethyl, 1-cyanoethyl or, if n is the number 1, also 2-cyanoethyl, R₂′ is C₁₋₄-alkyl, R₃ is cyanomethyl, cyanoethyl or C₃₋₆-carboalkoxymethyl, R₄ is hydrogen or chlorine, X$^\ominus$ is a colourless anion of an organic or inorganic acid and n is the number 0 or 1.

4. A benzimidazole according to claim 2 of the formula

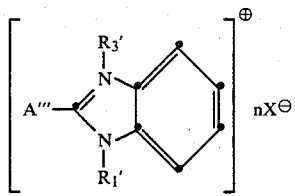

in which A‴ is the radical

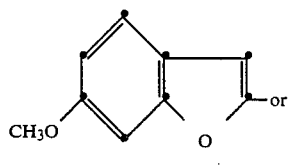

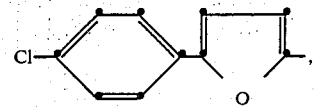

R₁′ and R₃′ independently of one another are cyanomethyl, or cyanoethyl R₃′ is C₃₋₆-carboalkoxymethyl and X$^\ominus$ is a colourless anion of an organic or inorganic acid.

5. A benzimidazole according to claim 4 of the formula

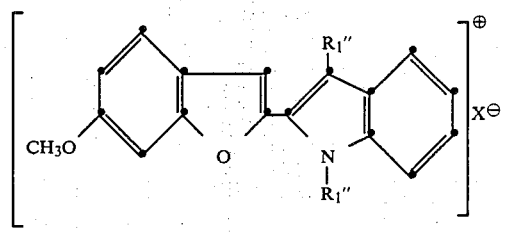

in which R₁″ is cyanoethyl and X$^\ominus$ is a colourless anion of an inorganic or organic acid.

6. A benzimidazole according to claim 4 of the formula

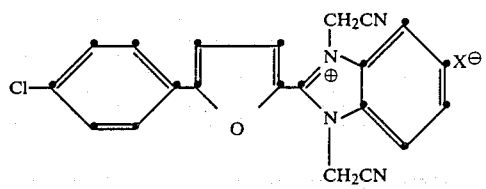

in which X$^\ominus$ is a colourless anion of an organic or inorganic acid.

7. The benzimidazole according to claim 3 of the formula

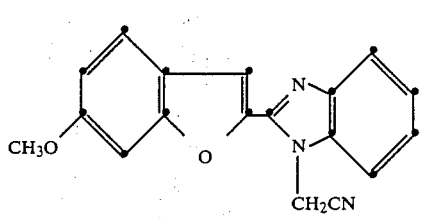

* * * * *